US010357617B2

(12) United States Patent
Holmqvist (10) Patent No.: US 10,357,617 B2
(45) Date of Patent: Jul. 23, 2019

(54) MEDICAMENT DELIVERY DEVICE COMPRISING A LOCKING MECHANISM (71) Applicant: Carebay Europe Ltd, Sliema (MT)

(72) Inventor: Anders Holmqvist, Värmdö (SE)

(73) Assignee: SHL Medical AG, Zug (CH)

(*) Notice: Subject to any disclaimer, the term of this patent is extended or adjusted under 35 U.S.C. 154(b) by 797 days.

(21) Appl. No.: 14/902,166

(22) PCT Filed: Mar. 12, 2014

(86) PCT No.: PCT/EP2014/054902
§ 371 (c)(1),
(2) Date: Dec. 30, 2015

(87) PCT Pub. No.: WO2014/154490
PCT Pub. Date: Oct. 2, 2014

(65) Prior Publication Data
US 2016/0303330 A1 Oct. 20, 2016

(30) Foreign Application Priority Data
Mar. 25, 2013 (SE) .................................. 1350376

(51) Int. Cl.
A61M 5/315 (2006.01)
A61M 5/20 (2006.01)
(Continued)

(52) U.S. Cl.
CPC .......... A61M 5/31571 (2013.01); A61M 5/20 (2013.01); A61M 5/24 (2013.01);
(Continued)

(58) Field of Classification Search
CPC .. A61M 5/31571; A61M 5/20; A61M 5/2033; A61M 5/31578; A61M 5/3257;
(Continued)

(56) References Cited

U.S. PATENT DOCUMENTS 8,376,985 B2 2/2013 Pongpairochana et al.
8,568,359 B2 10/2013 Carrel et al.
(Continued)

FOREIGN PATENT DOCUMENTS

CN 101868272 A 10/2010
CN 102821801 A 12/2012
(Continued)

OTHER PUBLICATIONS

English Translation of First Office Action issued in Chinese Patent Application No. 201480025608.8 dated Mar. 3, 2017.
(Continued)

Primary Examiner — Kami A Bosworth
Assistant Examiner — Alexandra Lalonde
(74) Attorney, Agent, or Firm — McDonnell Boehnen Hulbert & Berghoff LLP (57) ABSTRACT A medicament delivery device includes a tubular housing having opposite proximal and distal ends; an injection drive configured to exert force on a medicament container to expel medicament; and an injection drive holder configured to releasably hold the injection drive in a pre-tensioned state before injection of the medicament. The injection drive holder includes a tubular extension part for receiving the injection drive to be axially movable therein and a release ring coaxially arranged on the tubular extension part, the release ring being axially movable between proximal and distal positions along the outer surface of the tubular extension part. The tubular extension part is configured to engage with the injection drive when the release ring is at the proximal position and release the injection drive as the release ring moves distally from the proximal position.

17 Claims, 4 Drawing Sheets (51) Int. Cl.
*A61M 5/24* (2006.01)
*A61M 5/32* (2006.01)

(52) U.S. Cl.
CPC ...... *A61M 5/31578* (2013.01); *A61M 5/3202* (2013.01); *A61M 5/3205* (2013.01); *A61M 2005/208* (2013.01); *A61M 2005/2013* (2013.01); *A61M 2005/2073* (2013.01)

(58) Field of Classification Search
CPC .............. A61M 5/3243; A61M 5/3269; A61M 5/3271; A61M 5/31576; A61M 5/3219; A61M 2005/2073; A61M 2005/208; A61M 2005/2013; A61M 2005/206; A61M 2005/3267; A61M 2005/3268; A61M 2005/3217; A61M 2005/3257
See application file for complete search history.

(56) References Cited

U.S. PATENT DOCUMENTS

| | | | |
|---|---|---|---|
| 8,986,245 | B2 | 3/2015 | Karlsson et al. |
| 9,320,855 | B2 | 4/2016 | Holmqvist et al. |
| 2011/0196339 | A1 | 8/2011 | Hirschel et al. |
| 2011/0208126 | A1* | 8/2011 | Riemelmoser ...... A61M 5/3243 604/198 |
| 2012/0123350 | A1* | 5/2012 | Giambattista ....... A61M 5/2033 604/198 |
| 2015/0008541 | A1 | 1/2015 | Hong |
| 2016/0008541 | A1* | 1/2016 | Hirschel ............. A61M 5/2033 604/506 |

FOREIGN PATENT DOCUMENTS

| | | |
|---|---|---|
| DE | 10 2006 048180 A1 | 4/2008 |
| DE | 102006048180 A1 | 4/2008 |
| EA | 009030 B1 | 10/2007 |
| RU | 2438721 C2 | 1/2012 |
| TW | 201127433 A1 | 8/2011 |
| TW | 201244769 A1 | 11/2012 |
| WO | 02/47746 A1 | 6/2002 |
| WO | 2004/060445 A2 | 7/2004 |
| WO | 2006/118616 A1 | 11/2006 |
| WO | 2009/040602 A1 | 4/2009 |
| WO | 2011/099918 A1 | 8/2011 |
| WO | 2011/126439 A1 | 10/2011 |
| WO | 2011126439 A1 | 10/2011 |
| WO | 2012/105898 A1 | 8/2012 |
| WO | 2012105898 A1 | 8/2012 |
| WO | 2012122643 A1 | 9/2012 |
| WO | 2013/016832 A1 | 2/2013 |

OTHER PUBLICATIONS

EPO, Int'l Search Report in PCT/EP2014/054902, dated Dec. 15, 2014.
English Translation of Abstract of Russian Patent Application No. RU 2438721 dated Jan. 7, 2019.
Patent Examination Report No. 1 issued in Australian Patent Application No. 2014243350 dated Apr. 11, 2016.
Search Report issued in Taiwanese Patent Application No. 103110487 dated Aug. 30, 2016.
Translation of Official Action issued in Russian Patent Application No. 2015145464 dated Jan. 19, 2017.

* cited by examiner

MEDICAMENT DELIVERY DEVICE COMPRISING A LOCKING MECHANISM

This is the National stage filing under 35 U.S.C. 371 of the International Application PCT/EP2014/054902 filed Mar. 12, 2014 which claims benefit under 35 U.S.C. 119 (a-d) to SE1350376-8 filed Mar. 25, 2013.

The present invention relates to a medicament delivery device and, more specifically, to a medicament delivery device for auto-injection having a mechanism for inhibiting dose delivery until the device is positioned at a dose delivery site and/or for locking a needle guard in a proximal position to cover a needle after a dose is delivered. The device is a disposable single-use auto-injector with a fixed dose to be used as a platform device suitable for a range of dose formulations.

Medicament delivery devices for automatic or semi-automatic injection of medicaments have been known for many years. While the first generations of injectors merely aimed to deliver a medicament as quickly as possible, increased use of the devices by patients in non-clinical settings has lead to the necessity of providing further handling and safety functions.

Important handling and safety functions of medicament delivery devices include inhibiting premature actuation of the device (misfiring). To ensure that the medicament is properly injected, actuation of the device is inhibited until the auto-injector is correctly positioned at a dose delivery site. Furthermore, since the member delivering the medicament can be sharp and may be contaminated after the device has been actuated, devices that retract or cover the medicament delivery member when the device is withdrawn from the dose delivery site have been developed. To prevent a person from unintentionally contacting the medicament delivery member and to allow safe disposing of the device, some devices feature a mechanism that locks the device once the medicament delivery member is covered or retracted.

WO 02/047746 discloses a medicament delivery device comprising a housing arranged to contain a medicament container, a needle cover surrounding a needle and spring means. The spring means may push the needle past the end of the needle cover and operate the medicament container to supply a dose of medicament. Furthermore, the device comprises first locking means locking the spring means in a pressurized state. The first locking means may be released by first activating means, which may be manually operated. The first activating means are locked by second locking means, which are released by second activating means when the needle cover is exposed to pressure by the medicament delivery device being positioned at the dose delivery site. When the patient withdraws the injector from the dose delivery site, further spring means push the needle cover out of the housing. A lock ring having arms that engage openings in the housing is provided to prevent the needle cover being pushed in again. Although the medicament delivery device provides all necessary functions, quite a number of mechanism are necessary to achieve this objective.

WO 2004/060445 discloses a safety system for a syringe. The system may forcefully inject a syringe when an activator contacts the dose delivery site and withdraw the syringe into a housing when injection is completed. However, the needle and the guard can be moved, allowing for the needle to be contacted even after it is retracted into the housing. Therefore, WO 2004/060445 proposes the use of end covers for safe disposal of the system.

WO 2006/118616, which relates to a needleless injector device, discloses a mechanism for inhibiting actuation of the device until the device is positioned against the skin. However, also in this case the mechanism disclosed is not designed to prevent users or third persons from unintentionally contacting the medicament delivery member after the device is actuated.

As shown above, available medicament delivery devices do either not provide the necessary handling and safety functions or require cooperation of several complex mechanisms. Therefore, some of the presently available devices are not safe, while others are costly to produce, difficult to assemble and exposed to an increased risk of failure. Accordingly, there is a need for medicament delivery devices that comprise mechanisms providing some or all of these functions with as few parts as possible and in a reliable manner.

In order to overcome one or several of the above-mentioned problems, a medicament delivery device according to the independent claim(s) is provided.

Further aspects, improvements and variations are disclosed in the dependent claims, the figures and the description.

The medicament delivery device of the present invention allows inhibiting actuation of the device until the device is positioned at a dose delivery site. Furthermore, the medicament delivery member of the medicament delivery device is safely covered after actuation of the device. The device can thus be stored or discarded in a safe way. These advantages are achieved by providing a medicament delivery device with an improved locking mechanism. The locking mechanism of the inventive medicament delivery device provides one or several of the functions in a reliable and safe manner and requires a minimal amount of elements. The locking mechanism is easy to assemble so that the medicament delivery device can be manufactured cost-effectively. Furthermore, the medicament delivery device having the locking mechanism is less vulnerable to failure or malfunction.

In the present application, when the term "distal" is used, this refers to the direction pointing away from the dose delivery site. When the term "distal part/end" is used, this refers to the part/end of the delivery device, or the parts/ends of the members thereof, which is/are located farthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

A medicament delivery device comprises: a tubular housing having a proximal end and an opposite distal end; an injection drive configured to exert force on a medicament container to expel medicament; and an injection drive holder configured to releasably hold the injection drive in a pre-tensioned state before injection of the medicament. The injection drive holder may comprise a tubular extension part for receiving the injection drive to be axially movable therein and a release ring coaxially arranged on the tubular extension part. The release ring may be axially movable between proximal and distal positions along the outer surface of the tubular extension part. The tubular extension part may be configured to engage with the injection drive when the release ring is at the proximal position and release the injection drive as the release ring moves distally leaving the proximal position.

The medicament delivery device may further comprise a needle guard arranged to be biased in a proximal direction to cover a needle. The needle guard may be configured, when the device is applied and pressed on an injection site, to move distally exposing the needle and forcing the release ring in a distal direction.

Preferably, the tubular extension part comprises at least one release hook on an outer surface thereof. Preferably, the at least one release hook may be configured, in the proximal position, to be pressed radially inward by the release ring thereby engaging with a groove formed on the injection drive.

Further, the release hook may be configured to move outward to release the injection drive when the release ring leaves the proximal position moving distally.

Furthermore, the release ring may include at least one pair of lock arms extending in a proximal direction. The at least one pair of lock arms may be configured to engage with a corresponding slot formed on the outer surface of the tubular extension part when the release ring is at the proximal position.

In addition, the medicament delivery device may further comprise an activator arranged between the needle guard and the release ring. The activator may include at least one activation leg extending in a distal direction to correspond with the at least one pair of lock arms. Said at least one activation leg may be configured, when the activator is forced distally by the needle guard, to wedge in between said pair of lock arms, thereby unlocking the lock between the lock arms and the slot.

Moreover, said at least one pair of lock arms may be arranged on opposite sides of the release ring and said at least one activation leg is arranged correspondingly on the activator.

Besides, the medicament delivery device may further comprise a medicament container holder coaxially arranged within the needle guard and the activator. The medicament container holder may have on an outer surface thereof an activator holding member for holing the activator in place. The activator holding member may be releasably engageable with a corresponding holding member provided on the activator.

Additionally, two of said corresponding holding members may be respectively arranged at proximal and distal positions on the activation leg to be snap-fittable with the activator holding member of the medicament container holder at two different positions longitudinally spaced apart from each other.

Preferably, the medicament delivery device may further comprise a locking mechanism including a lever provided on the medicament container holder. The lever may be configured to prevent movement of the needle guard in a proximal position after actuation of the device.

Further, the lever may include a proximal portion, an opposite distal portion and a pivotal axis arranged between the proximal and distal portions, about which the lever can pivot.

Furthermore, the distal portion of the lever may be configured to be pressed inward by the activator when the activator is moved in the distal direction by the needle guard.

Moreover, the distal portion of the lever may be configured to be kept being pressed inward by the activator when the needle guard is moved back to the proximal position after actuation of the device.

Besides, the activator holding member of the medicament container holder may be configured to, when the activator is moved in the distal direction, snap-fit one of said corresponding holding member arranged at the proximal position.

Additionally, the injection drive may comprise a plunger rod accommodated at least partly within the injection drive holder and a spring arranged within the plunger in a pre-tensioned state before injection of the medicament.

A medicament delivery device according to the present invention comprises a needle guard for covering a needle from sight. In the context of the present invention, the term "needle guard" or "guard" denominates a member for covering a medicament delivery member. The guard preferably is contacted when the device is positioned at the dose delivery site. Furthermore, the guard preferably covers the medicament delivery member when the device is withdrawn from the dose delivery site at least after the device has been actuated. Preferably, after actuation of the device the guard is moved to and locked in a position covering the medicament delivery member. Hence, the guard according to the invention is movable or displaceable. More preferably, after the device has been actuated, the guard is moved in a proximal direction and locked against a further distal movement when the device is withdrawn from the dose delivery site. The guard preferably is urged in a distal direction by the force of a spring. The spring may be provided at the distal side of the guard. The spring may be formed integrally with the guard. Thus, the guard is a protection element, such as a needle protection element or needle protection sleeve that protects the user against inadvertently or accidentally getting in contact with the needle which may be contaminated.

A medicament delivery member may be any member through which a medicament is delivered. For example, the medicament delivery member may be a needle or a nozzle, e.g., a needle-less injection nozzle. The medicament delivery member may be formed integrally with a medicament container or be an independent element of the device. Preferably, the medicament delivery member is covered or retracted until the medicament delivery device is actuated and may not be unintentionally contacted until this moment. For example, the medicament delivery member may be retracted in the medicament delivery device.

According to any embodiment of the present invention, the medicament delivery device may comprise an actuation mechanism and/or an activator. An actuation mechanism is a mechanism that actuates the device to deliver a dose. Preferably, the actuation mechanism actuates the device by releasing spring means from a pressurized state, the spring means being capable of generating force for pressing the medicament container to eject the medicament through the medicament delivery member to provide a dose of medicament. Preferably, the actuation mechanism actuates the device when activated by a user. The actuation mechanism preferably is activated when the user presses the device on an injection site without requiring any additional operation by the user.

In any embodiment of the present invention, the actuation mechanism preferably can only be activated when certain conditions are fulfilled. Preferably, the actuation mechanism is locked and can not be actuated until the device is applied at a dose delivery site. For this purpose the device may comprise an activator holing mechanism. The activator holding mechanism may prevent actuation of the device by locking the actuation mechanism and/or by locking another member and thereby inhibiting that the actuation mechanism is activated (e.g., unintentionally). Preferably, the activator holding mechanism locks actuation of the device by restricting the movement of a member or part of the actuation mechanism or of the entire actuation member. For example, the activator holding mechanism may comprise a snap-fitting bump-and-groove combination. Preferably, the activator holding mechanism comprises at least one first holding position for holding of the activator before delivery of medicament and at least one second position for holding after delivery of medicament.

In any embodiment of the present invention the actuation mechanism and/or the activator may be provided such that actuation of the medicament delivery device is inhibited until the device is positioned at the dose delivery site. Preferably, actuation of the device is inhibited until a guard, e.g., a needle protection sleeve, that contacts the dose delivery site is moved, displaced or retracted and reaches a distal position.

Any embodiment of the present invention may be provided with a locking mechanism. The locking mechanism of the embodiment may comprise a lever. The lever may be a see-saw. The lever may have the form of a longitudinally extending beam, pivoted to the medicament container holder. Preferably, the distal end of the beam is arranged with an outward protrusion. The protrusion has at least one side surface forming an acute angle with the longitudinal direction of the device so that a member of the actuation mechanism can slide thereon. The surface may face towards the proximal end of the device.

According to any embodiment of the invention the actuation mechanism may comprise a medicament delivery drive unit for expelling the medicament from the medicament delivery device. The drive unit may include a plunger member. At least one spring for spring-loading the plunger member may be provided around the plunger member or in a hollow space thereof. The plunger member may be spring-loaded by the spring being compressed or elongated.

The medicament delivery drive unit may further comprise a drive holder for holding the spring-loaded plunger member in a pre-loaded state. For this purpose the drive holder may comprise a flexible hook which may be pressed inward in the radial direction. The hook may be configured to fit into at least one cut-out of the plunger member or a plunger rod. The drive holder may be configured to partially surround the spring-loaded plunger member. Further, the drive holder may comprise a tubular member and at least one member coaxially slidable thereon. The at least one member of the drive holder may be arranged surrounding the tubular member such that the flexible hooks of the tubular member are engaged in a corresponding engagement with a cut-out on the plunger member. Preferably, the at least one member is configured to release the tubular member from the spring-loaded plunger member or the plunger rod by sliding on the tubular member.

Preferably, the drive unit comprises a drive spring holder having a generally U-shape. The drive spring holder may have at least one, preferably two proximally directed leg. Each leg may comprise a radial outwardly extending ledge. The drive spring holder may be arranged to at least partially surround the spring-loaded plunger member. Preferably, the drive spring is compressed between a proximal inner end surface of the plunger member and drive spring holder when the medicament delivery drive unit is assembled. More preferably, the drive spring is compressed between a proximal inner end surface of the plunger member and a transversal contact end of the drive spring holder. The radial outwardly extending ledges of the of the drive spring holder may be engaged to the proximal annular surface of the tubular member for preventing the drive spring holder from being moved in the distal direction by the spring. Further, the drive spring holder may be configured to generate audible and/or tactile and/or visible confirmation signal when released from the tubular member.

The following Figures below disclose an embodiment of the invention for illustrational purposes only. In particular, the disclosure within the Figures is not meant to limit the range of protection of the invention. The embodiment shown may be modified in many ways within the scope of the claims.

Figure 1:
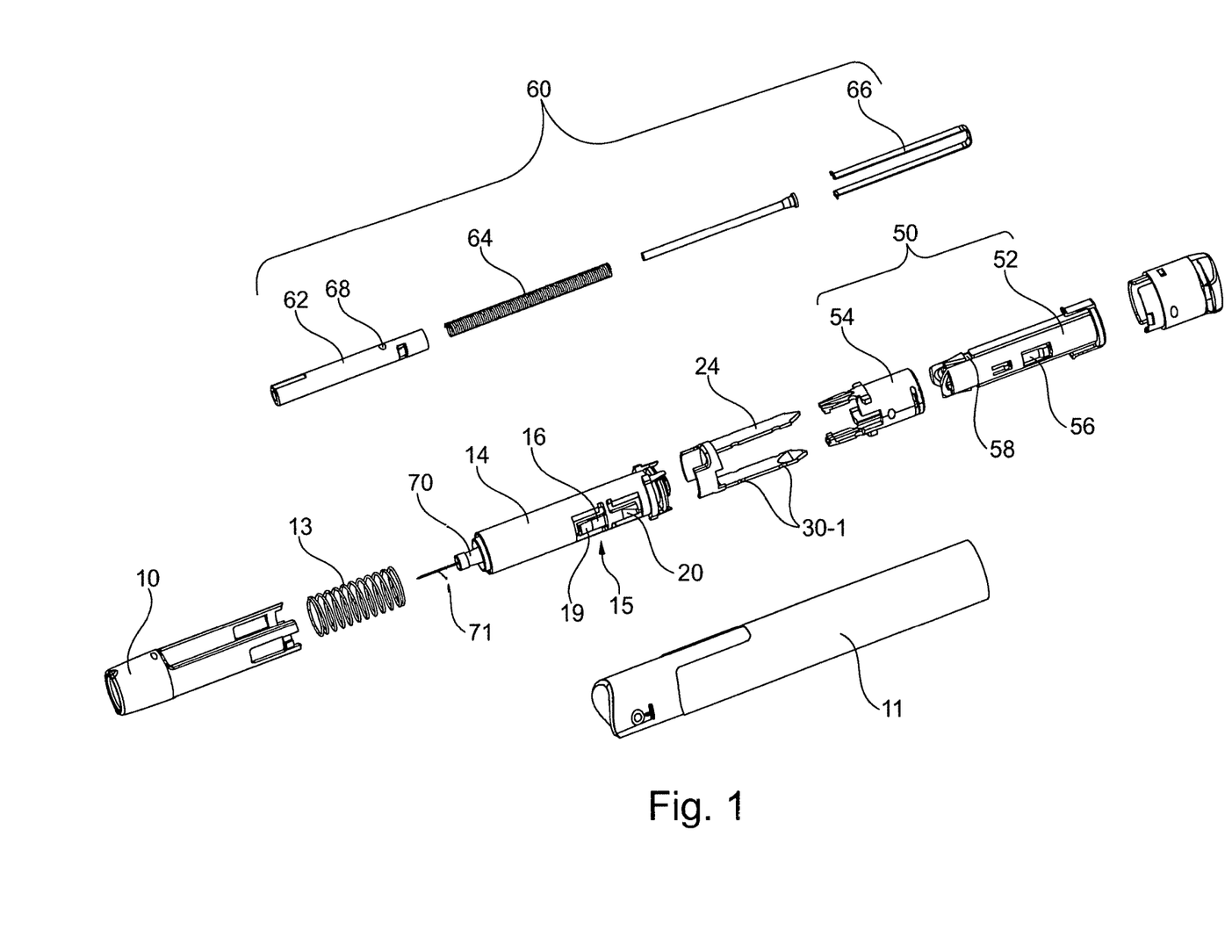
FIG. 1: Exploded view of the medicament delivery device of the present invention.

FIG. 1 shows an exploded view of a medicament delivery device according to one embodiment of the present invention. The device comprises a needle guard 10 or sleeve-like structure slidable in the longitudinal direction inside a generally cylindrical housing 11. A spring 13 may be arranged for urging the needle guard 10 in the proximal direction.

Figure 2:
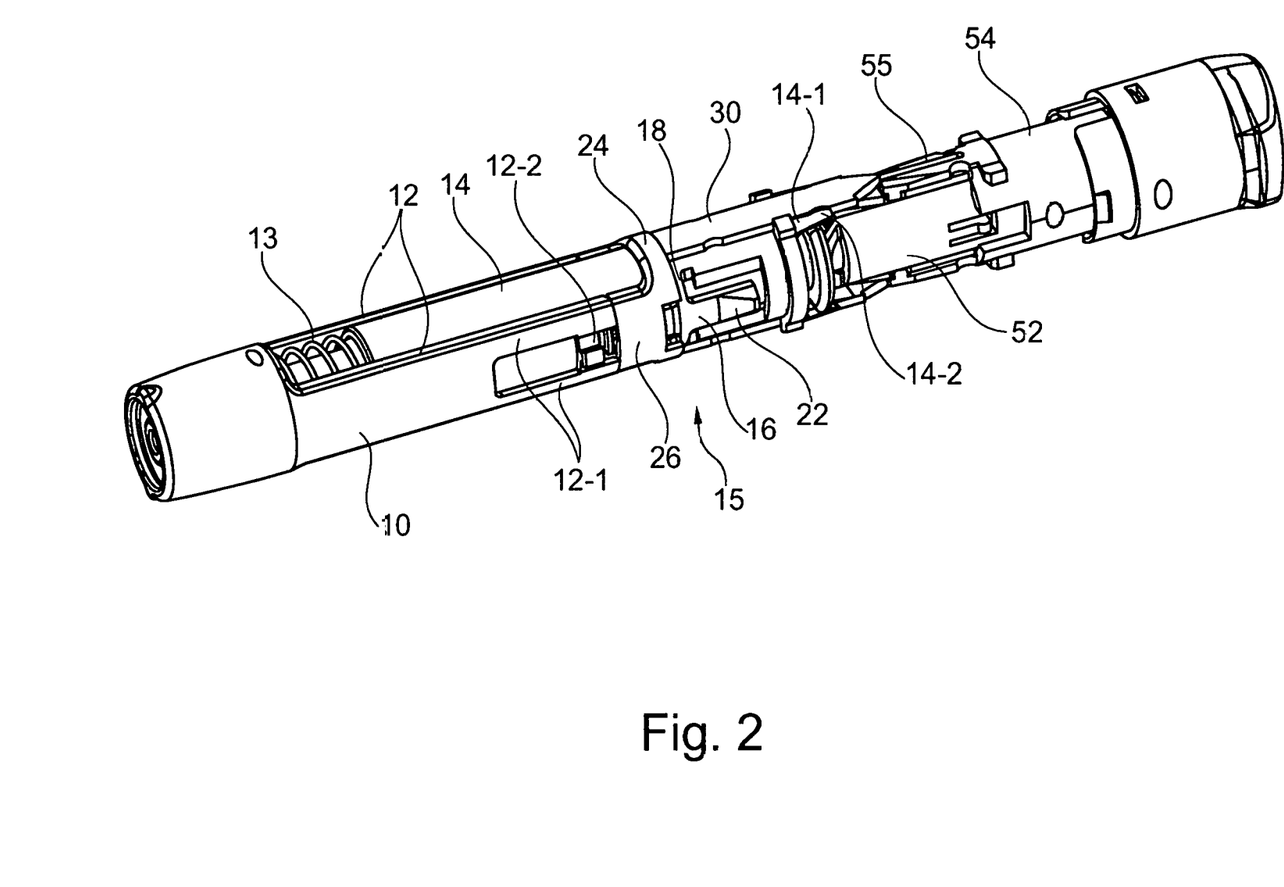
FIG. 2: A perspective view of an embodiment of a medicament delivery device of the present invention before delivery of the medicament.

The needle guard 10 may comprise a generally tubular part at its proximal end and at least one distally directed leg. For example, as shown in FIG. 2, the needle guard 10 may comprise at least two distally directed legs 12 extending from the proximal tubular part. Further, the leg 12 has two tongues 12-1 extending in the distal direction from opposite sides thereof. At or near the distal end of the two tongues 12-1 is provided a bridge 12-2 connecting the two tongues. A medicament container holder 14 for holding a medicament container 70 may be arranged inside the needle guard 10. The medicament container 70 may comprise a medicament delivery member. However, the medicament delivery member does not have to be part of the medicament container and may be an independent element of the device. As shown in FIG. 1, the medicament delivery member may be a needle 71.

A side surface of the medicament container holder 14 may be arranged with a locking mechanism 15. The locking mechanism 15 of the embodiment comprises a lever. The lever may be a see-saw. The lever may have the form of a longitudinally extending beam 16. The beam 16 may be connected at the middle thereof to the medicament container holder 14 by two pivot arms 18, consequently having a proximal end 19 and a distal end 20. The beam may be formed integral with the medicament container holder 14 or pivotally engaged therewith. The distal end 20 of the beam 16 may be arranged with an outward protrusion 22. Preferably, the protrusion 22 has a proximal side surface, a surface facing towards the proximal end of the device, forming an acute angle with the longitudinal direction. The needle guard 10 may be in such an arrangement with respect to the beam 16 that the two tongues 12 are positioned on each side of the beam 16 without overlapping, as will be explained further below. The medicament container holder 14 may have at least one arm 14-1 on an outer surface thereof. The shown embodiment comprises two arms 14-1 arranged at opposite sides of the medicament container holder 14. The arms 14-1 are provided with an activator holding member 14-2, e.g., a bump in the embodiment, for holding an activator 24 in place, as will be detailed below.

Furthermore, the device may be provided with an activator 24. The activator 24 may comprise a generally ring-shaped or sleeve-shaped part 26 surrounding the medicament container holder 14 and positioned distally in relation to the needle guard 10. The ring-shaped part 26 may have at least one distally directed activation leg 30, preferably two legs on opposite sides, as in the shown embodiment. As depicted in FIG. 2, the legs 30 may have pointed distal ends, which are arranged to wedge in between a pair of lock arms 55 of a release ring 54 by making a sliding movement in the distal direction during the activation of the device. Further, on each side of the legs 30 are arranged two grooves 30-1 as holding members, one near the proximal end of the leg 30, i.e., close to the ring-shaped part 26, and the other near the distal end of the leg 30, i.e., close to the pointed end. These two pairs of grooves 30-1 at proximal and distal positions of the legs 30 are formed to correspond with the bumps 14-2 arranged on the arms 14-1 of the medicament container holder 14 so that the bumps 14-2 can snap-fit the grooves 30-1. Preferably, the bump-groove-snap-fit structure is designed to meet certain strength requirements. For instance, the snap-fit should be strong enough to hold the weight of the activator legs 30 during a standardized drop test so as to prevent an unintentional misfiring. Further, the snap-fit should be as weak as possible to reduce the force required to retract and move the needle guard 10 and the activator 24 in the distal direction. In the meantime, the grooves arranged at the distal position engages with the bumps 14-2 in the initial state, and the grooves at the proximal position engages with the bumps 14-2 when the device is activated, i.e., when the activator 24 is moved distally.

At the distal direction of the activator 24 is arranged a drive holder, e.g., an injection drive holder 50, for releasably holding a drive, e.g., an injection drive 60, in a pre-tensioned state before injection of the medicament. The injection drive holder 50 may comprise a tubular extension part 52 and a release ring 54 coaxially arranged thereon. The tubular extension part 52 accommodates at least a part of the injection drive 60 therein to be axially movable. In order to hold the injection drive 60 in place, the tubular extension part 52 comprises at least one release hook 56, preferably two on opposite sides, arranged on an outer surface thereof. The release hook 56 is flexible and can be pressed inward by the release ring 54 when the release ring 54 rides thereon, thereby locking the injection drive 60 in place before injection of the medicament. At the outer surface of the tubular extension part 52 is arranged at least one slot 58, preferably two slots at opposite sides, for engaging with and locking the release ring 54. According to the embodiment, the slot 56 extends in a direction perpendicular to the longitudinal direction of the device and is arranged at different sides from the release hooks 56, preferably approximately 90 degrees away along the circumference of the tubular extension part 52, in order to avoid any interference therebetween. In the meantime, the release ring 54, surrounding the tubular extension part 52, is axially movable along the outer surface of the tubular extension part 52 when it is not locked with the slot 58 on the tubular extension part 52. The release ring 54 may comprise a generally tubular distal part arranged with at least one pair of lock arms 55, preferably two pairs on opposite sides, extending in the proximal direction. The two lock arms 55 forming one pair have a small interval between them running in the longitudinal direction. The interval can be of any size as long as the pointed end of the activator leg 30 can wedge in therethrough when the activator 24 is forced distally by the needle guard 10. Further, each of the lock arms 55 has a radially inward protrusion which can engage with the slot 58 formed on the tubular extension part 52 to lock longitudinal movement of the release ring 54.

The injection drive 60 may comprise a plunger member or an elongated plunger rod 62. The plunger member may be provided with a hollow space into which a drive spring 64 is arranged to spring-load the plunger member. The proximal end of the elongated plunger rod 62 may be in contact with a stopper of the medicament container 70. The injection drive 60 may further comprise a drive spring 64 acting on the plunger rod 62. A distal end of the drive spring may be in contact with a drive spring holder 66 having a general U-shape. A signal generating member of the embodiment may comprise, e.g., the drive spring holder 66, which is an elongated U-shaped bracket, provided with longitudinally directed legs and each leg may include a radial outwardly extending ledge. The drive spring holder 66 may be configured to at least partially surround the spring-loaded plunger member. When the injection drive 60 is in the pre-tensioned state, the distal end of the drive spring holder 66 is arranged at a predetermined distance "D" from an inner distal surface of said tubular extension part 22 and when the injection drive 60 is in the released state, the distal end of the U-bracket 66 is in contact with the inner distal surface of said tubular extension part 22. The audible and/or tactile and/or visible confirmation signal is generated when the distal end of the U-bracket 66 hits and contacts the inner distal surface of the tubular extension part 22 by a remaining force exerted by said drive spring 64.

When the medicament delivery drive unit is assembled, the drive spring 64 may be compressed between a proximal inner end surface of the plunger member and a transversal contact end of the drive spring holder 66. The radial outwardly extending ledges of the drive spring holder 66 may be engaged with the proximal annular surface of the tubular extension part 52 for preventing the drive spring holder 66 from being moved in the distal direction by the force exerted from the drive spring 64. The release ring 54 may be arranged surrounding said tubular extension part 52 at a (proximal) position where the at least one pair of lock arms 55 of the release ring 54 engage with the slot 58 on the tubular extension part 52. At this position, the release hook 56 of the tubular extension part 52 is pressed inward by an overlapping inner surface of the release ring 54 so as to engage with a groove, e.g., cut-out 68, formed on an outer circumference of the plunger rod 62, thereby preventing longitudinal movement of the injection drive 60 before activation of the device.

As shown in FIG. 2, in the initial state, since the lock arms 55 of the release ring 54 are engaged with the slot 58 on the tubular extension part 52 through their inward protrusions, axial movement of the release ring 54 is prevented. At the same time, since the release ring 54 at this position presses the release hooks 56 inwardly, the tubular extension part 52 locks the plunger rod 62 in place. In the meantime, the needle guard 10 and the activator 24 are also in their initial position so that the distal grooves 30-1 of the activator 24 engage with the bumps 14-2 on the medicament container holder arms 14-1. Accordingly, the activator 24 is inhibited from distal movement. This holding of the activator 24 secures the locking between the release ring 54 and the tubular extension part 52.

Figure 3:
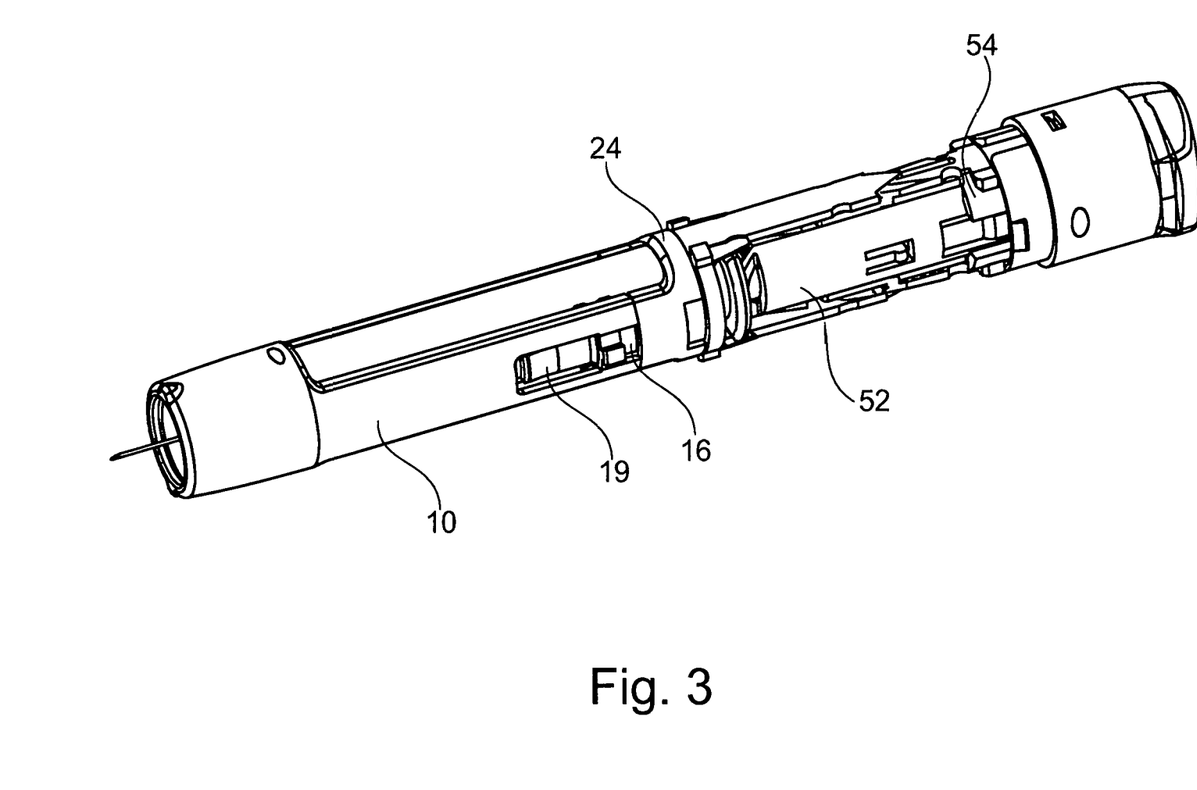
FIG. 3: A perspective view of an embodiment of a medicament delivery device of the present invention in an actuated state.

The next step is to perform a dose delivery. This is done by pressing the proximal end of the needle guard 10 against a dose delivery site. This causes the needle guard 10, together with the activator 24, to slide in the distal direction of the device, whereby the distally directed legs 30 of the activator 24 move distally into the small interval between the pair of lock arms 55. As the activator 24 slides further distally, the pointed end of the activator leg 30 wedge in between the pair of lock arms 55 of the release ring 54. This forces the lock arms 55 to opposite sides of the slot 56, and finally disengages them from the slot 56. Now, further distal movement of the activator 24 can push the release ring 54 toward the distal end of the device. When the release ring 54 is moved a specified distance in the distal direction, it leaves the release hooks 56 of the tubular extension part 52 that have been pressed in to hold the injection drive 60. As the release hooks 56 move outwards, the injection drive 60, i.e., the plunger rod 62 and the drive spring 64 in the pre-tensioned state, is released from the locked state. The plunger rod 62 may then be forced in the proximal direction by the drive spring 64 and may act on the stopper inside the medicament container 70 so as to deliver a dose of medicament through the medicament delivery member at the dose delivery site. Thus, delivery of a dose of medicament is initiated. In the meantime, as the activator 24 slides distally, it rides on the outward protrusion 22 of the beam 16 along the acute angled proximal side surface thereof. This forces the distal end 20 of the beam 16 to be pressed inwardly, thereby building up tension in the beam 16, which will be used in the later stage of the device operation to lock the needle guard 10 in place.

In the meantime, during the delivery procedure, when the distal end of the plunger rod 62 passes by the U-shaped bracket 66—the radial outwardly extending ledges of the U-shaped bracket 66, to be exact—, the drive spring holder 66 is released and allowed to move in the distal direction by a remaining force exerted by said drive spring 64. When the U-bracket 66 hits the distal end of the tubular extension part 22, a signal, typically an audible sound and/or a visual signal and/or a tactile signal is generated.

Figure 4:
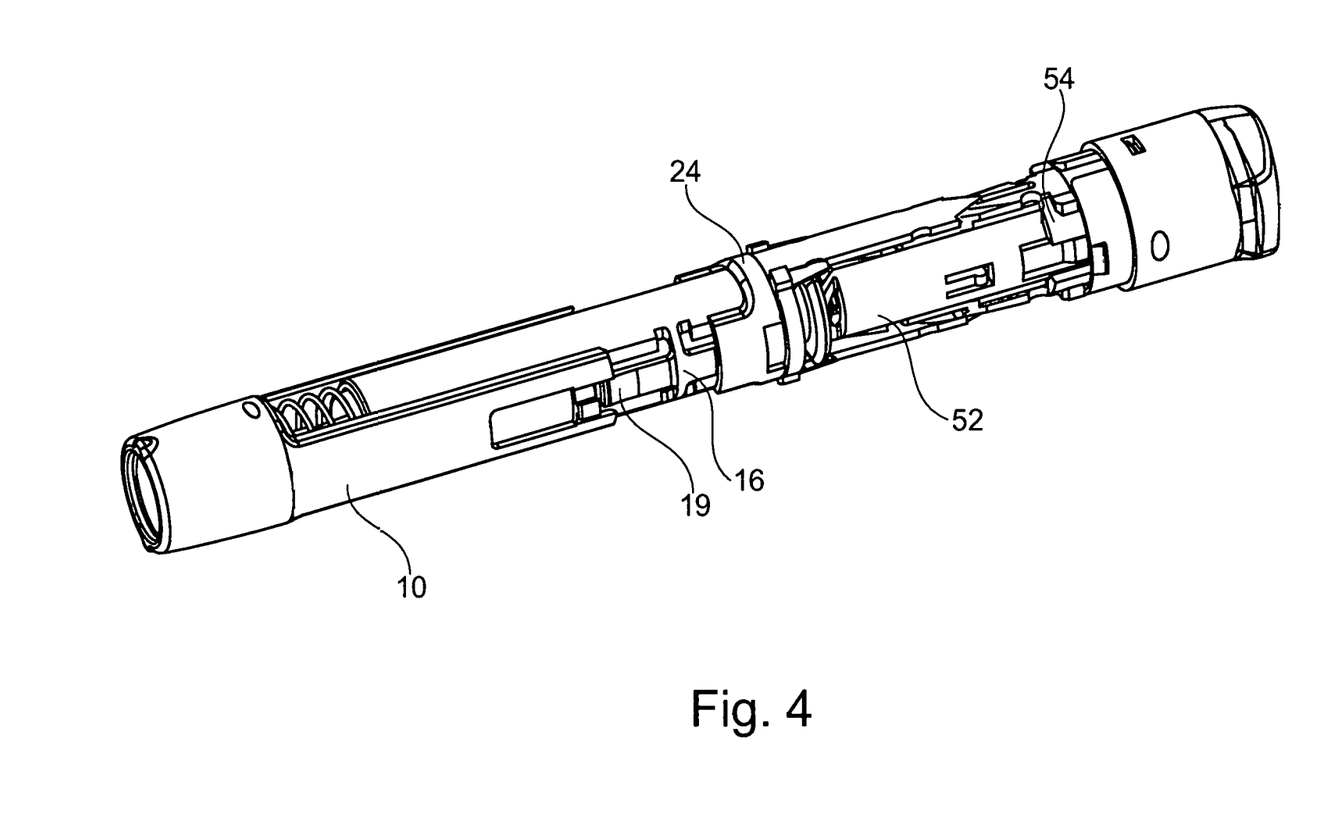
FIG. 4: A perspective view of an embodiment of a medicament delivery device of the present invention after use.

When the stopper has reached its end position, i.e. the proximal end position, inside the medicament container 70, the medicament delivery operation is completed. Upon the completion of the delivery, the device may be withdrawn from the dose delivery site. This in turn may cause the needle guard 10 to be moved in the proximal direction by the spring 13. The proximal movement by the spring 13 will cause the needle guard 10 to release the proximal end 19 of the beam 16 which has been pressed inward during the injection operation by the overlapping part of the needle guard 10. Thus, the proximal end 19 of the beam 16 will flex outwards in the radial direction due to the tension built up in the beam 16 by the protrusion 22 at the distal end 20 being kept pressed inwards by the activator 24. The lever, preferably beam 16, may thus reach the final position shown in FIG. 4 in which the lever restricts the movement of needle guard 10 in the distal direction. The proximal end 19 of the longitudinal beam 16 may be positioned between the two tongues 12-1 of the needle guard 10 engaging the distal side of the bridge 12-2, thereby locking the needle guard 10 against movement in the distal direction and allowing the device to be discarded safely.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device, comprising:
a tubular housing having a proximal end and an opposite distal end;
a drive configured to exert force on a medicament container to expel medicament; and
a drive holder configured to releasably hold the drive in a pre-tensioned state before delivery of the medicament;
wherein the drive holder comprises a tubular extension part configured to receive the drive such that the drive is axially movable therein, and a release ring coaxially arranged on the tubular extension part, the release ring being axially movable between proximal and distal positions along an outer surface of the tubular extension part,
wherein the tubular extension part is configured to engage with the drive when the release ring is at the proximal position and to release the drive as the release ring moves distally from the proximal position, and
wherein the release ring includes a distal part arranged with at least one pair of lock arms extending in a proximal direction from the distal part towards a proximal end of the medicament delivery device, the at least one pair of lock arms being configured to engage with a corresponding slot formed on the outer surface of the tubular extension part when the release ring is at the proximal position.

2. The medicament delivery device of claim 1, wherein the tubular extension part comprises at least one release hook on the outer surface of the tubular extension part; and in the proximal position, the at least one release hook is configured to be pressed radially inward by the release ring, thereby engaging with a groove on the drive.

3. The medicament delivery device of claim 2, wherein the at least one release hook is configured to move outward to release the drive when the release ring moves distally from the proximal position.

4. The medicament delivery device of claim 1, further comprising a needle guard arranged to be biased in the proximal direction to cover a needle, wherein the needle guard is configured to move distally, exposing the needle and forcing the release ring in a distal direction, when the medicament delivery device is applied and pressed on a delivery site.

5. The medicament delivery device of claim 4, wherein the tubular extension part comprises at least one release hook on the outer surface of the tubular extension part; and in the proximal position, the at least one release hook is configured to be pressed radially inward by the release ring, thereby engaging with a groove on the drive.

6. The medicament delivery device of claim 5, wherein the release hook is configured to move outward to release the drive when the release ring moves distally from the proximal position.

7. The medicament delivery device of claim 4, further comprising an activator arranged between the needle guard and the release ring, the activator including at least one activation leg extending in a distal direction to correspond with the at least one pair of lock arms, wherein the at least one activation leg is configured to wedge in between the at least one pair of lock arms, when the activator is forced distally by the needle guard, thereby unlocking the at least one pair of lock arms and the slot.

8. The medicament delivery device of claim 7, further comprising a medicament container holder coaxially arranged within the needle guard and the activator; wherein the medicament container holder has on an outer surface thereof an activator holding member for holding the activator in place; and the activator holding member releasably engages a corresponding holding member provided on the activator.

9. The medicament delivery device of claim 7, wherein the at least one pair of lock arms are arranged on opposite sides of the release ring, and the at least one activation leg is arranged correspondingly on the activator.

10. The medicament delivery device of claim 9, further comprising a medicament container holder coaxially arranged within the needle guard and the activator; wherein the medicament container holder has on an outer surface thereof an activator holding member for holding the activator in place; and the activator holding member releasably engages a corresponding holding member provided on the activator.

11. The medicament delivery device of claim 10, wherein the corresponding holding member provided on the activator is a distal holding member arranged at a distal position on the at least one activation leg, wherein the activator further comprises a proximal holding member arranged at a proximal position on the at least one activation leg, the distal holding member and the proximal holding member provided on the at least one activation leg for snap-fit with the activator holding member of the medicament container holder at two different positions longitudinally spaced apart from each other.

12. The medicament delivery device of claim 11, further comprising a locking mechanism including a lever provided on the medicament container holder, wherein the lever is configured to prevent movement of the needle guard when the needle guard is in a proximal position after actuation of the medicament delivery device.

13. The medicament delivery device of claim 12, wherein the lever includes a proximal portion, an opposite distal portion, and a pivot axis arranged between the proximal and distal portions, about which the lever pivots.

14. The medicament delivery device of claim 13, wherein the distal portion of the lever is configured to be pressed inward by the activator when the activator is moved in the distal direction by the needle guard.

15. The medicament delivery device of claim 14, wherein the distal portion of the lever is configured to be kept pressed inward by the activator when the needle guard is moved back to the proximal position after actuation of the medicament delivery device.

16. The medicament delivery device of claim 14, wherein the activator holding member of the medicament container holder is configured to snap-fit to the proximal holding member when the activator is moved in the distal direction.

17. The medicament delivery device of claim 1, wherein the drive comprises a plunger rod accommodated at least partly within the drive holder and a spring arranged within the plunger rod in a pre-tensioned state before delivery of the medicament.

* * * * *